United States Patent [19]
Cauley et al.

[11] Patent Number: 5,830,651
[45] Date of Patent: Nov. 3, 1998

[54] HUMAN OLIGODENDROGLIAL PROGENITOR CELL LINE

[75] Inventors: Keith Cauley, Burlington, Vt.; Válery Kukekov, San Diego, Calif.

[73] Assignee: Signal Pharmaceuticals, Inc., San Diego, Calif.

[21] Appl. No.: 458,890

[22] Filed: Jun. 1, 1995
(Under 37 CFR 1.47)

[51] Int. Cl.$^6$ ................ C12Q 1/68; C12N 5/10
[52] U.S. Cl. .............. 435/6; 435/368; 435/392; 435/402
[58] Field of Search ............. 435/6, 368, 392, 435/402; 424/93.21, 93.7

[56] References Cited

PUBLICATIONS

Duncan J. Neurochem., vol. 64 (1995) p. 529, abstract C.
Noble et al. The 0–2A Lineage; From Rats to Humans. Recent Results in Cancer Research. 1994, vol. 135, pp. 67–75.
Lubetzki et al. Gene Transfer of Rat Mature Oligodendrocytes and Glial Progenitor Cells with the LaxZ Gene. Ann. N.Y. Acad. Sci. 1990, vol. 605, pp. 66–70.

Tenebaum et al. Adeno–Associated Virus (AAV) as a Vector for Gene Transfer Into Glial Cells of the Human Central Nervous System. Gene Therapy. 1994, vol. 1, Suppl. 1, p. S80.

Noble et al. From Rodent Glial Precursor Cell to Human Glial Neoplasia in the Oligodendrocyte–Type–2 Astrocyte Lineage. Glia. 1995, vol. 15, pp. 222–230.

Kukekov et al. Characterization of a Perpetuated Human Oligodendroglial Progenitor Cell Culture. Society for Neuroscience Abstracts. 1995, vol. 21, pp. 319, abstract No. 134.3.

Espinosa et al. Oligodendroglial Progenitors Grafted in an Ectopic Location Migrate and Integrate in a histo type Manner in the Developing Rat Cerebellum. Journal of Neurochemistry. 1995, vol. 64, p. S29, abstract D

*Primary Examiner*—James Ketter
*Attorney, Agent, or Firm*—Fish & Richardson P.C.

[57] ABSTRACT

A human pre-oligodendroglial stem cell line, HOP-1, is provided herein. The cell line is useful for methods of treatment of central nervous system disorders, as well as for neuropharmaceutical drug discovery.

29 Claims, 4 Drawing Sheets

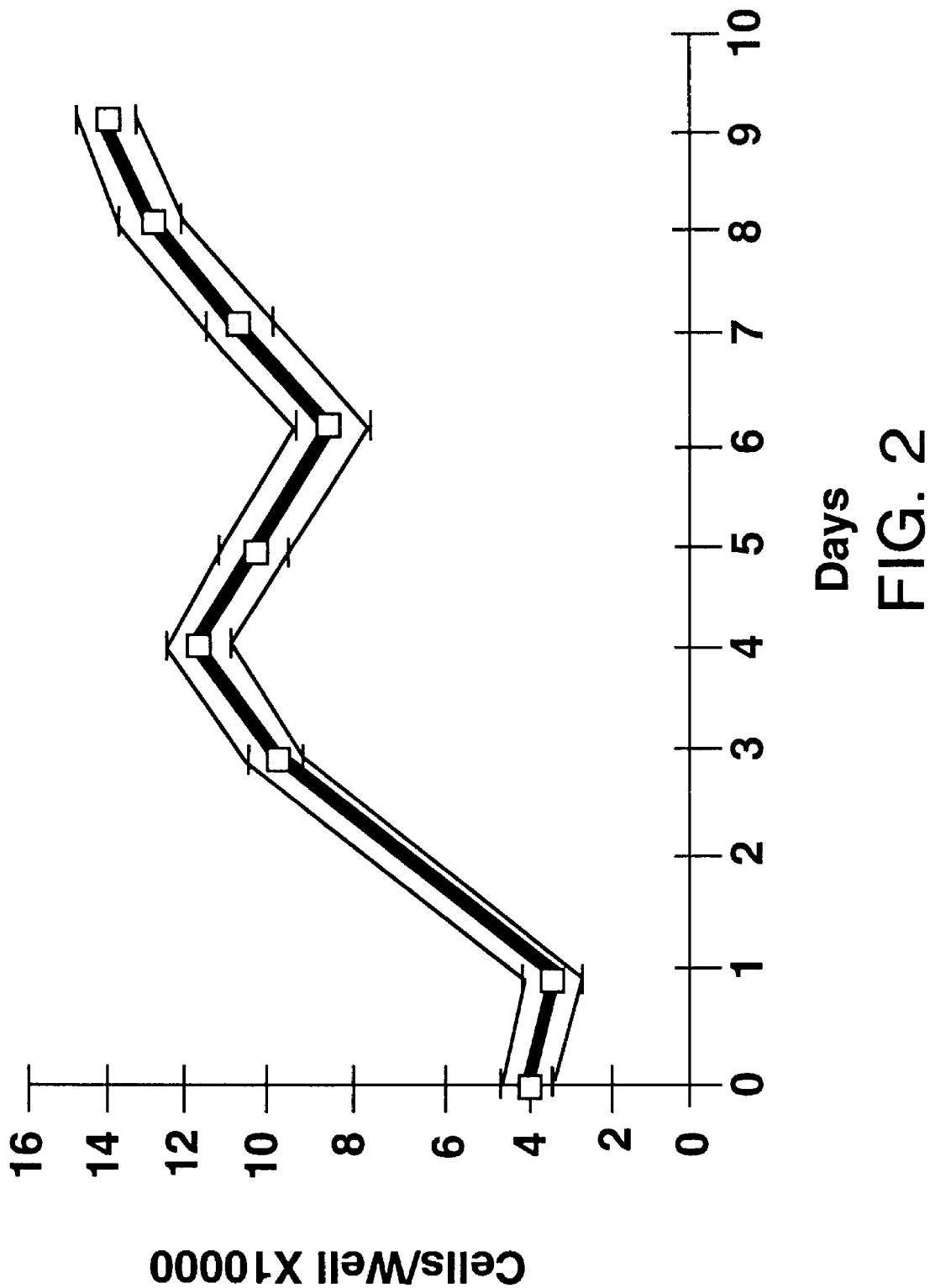

HUMAN OLIGODENDROGLIAL PROGENITOR CELL LINE

BACKGROUND OF THE INVENTION

1. Field of the Invention

This invention relates generally to neurobiology and specifically to the isolation of a human oligodendroglial progenitor stem cell line (HOP-1) having characteristics of bipotential oligodendroglial progenitor cells, and methods of use therefor.

2. Description of Related Art

Cells of the central nervous system (CNS) are broadly classified as either neurons or glial cells. Glial cells can be further subdivided into astrocytes and oligodendrocytes. Only a few CNS cell types have been reported to divide in the adult brain and these cells do not survive well in vitro. To date, most procedures that exist to establish cell lines from the CNS and neuronal tissues require oncogenic or retroviral means for immortalization, which raises questions of significant change in gene expression as a result of transformation.

There are hundreds of different types of cells in the CNS and many different neurotrophic factors which influence their growth and differentiation. Depending on the type of cell and the region of the brain in which the cell resides, a different neurotrophic factor or specific combination of factors affect the survival, proliferation and differentiation of the cell in vivo. Each type of cell responds to different combinations of neurotransmitters, neurotrophic factors, and other molecules in its natural environment. To date, neuropharmacological studies on the CNS have been delayed by the lack of appropriate cell systems for investigating and identifying potentially useful neuroactive compounds. In live animals, the complexity of the brain makes it difficult to effectively measure which cellular receptors are being targeted by these compounds. Additionally, the expense involved in live animal research and the current controversies stemming from animal rights movements have made in vivo animal studies less acceptable for initial research.

Primary cells from neural tissue are often used for CNS studies, however, fresh dissections must be performed for each study in order to obtain the necessary neuronal and glial cell types. This results in increased costs and increased variability in the experimental results. In the past, establishment of neural cell lines had proven so elusive that it is generally accepted by the scientific community that cells of CNS origin cells do not proliferate in vitro.

While some neuronal and glial tumorigenic cells exist, they are few in number and are not well characterized. In general, these tumor cell lines do not mimic the biology of the primary cells from which they were originally established and, as a result, are not suitable for drug discovery screening programs. In vitro primary cultures that would be more phenotypically representative of primary cells and that could be used to generate continuous cultures of specific cell lines capable of proliferation would be invaluable for neurobiological studies and CNS drug discovery efforts, as well as therapy.

It has become increasingly apparent that more defined conditions and further refinements in culture methodology are necessary to produce CNS cell lines which would enhance the yield of information from in vitro studies of the nervous system. Recognition of cell type and developmental stage-specific requirements for maintaining neural cells in culture as well as the development of a broader range of culture conditions are required. However, in order to achieve these goals it is critical to develop optimal culture methods that mimic in vivo conditions which are devoid of the biological fluids used in conventional culture techniques.

Recently, several researchers have isolated and immortalized progenitor cells from various regions of the brain and different stages of development. Olfactory and cerebellum cells have been immortalized using the viral myc (v-myc) oncogene to generate cell lines with neuronal and glial phenotypes (Ryder, et al., *J Neurobiology,* 21:356, 1990). Similar studies by Snyder, et al. (*Cell,* 68:33,1992) resulted in multipotent neuronal cell lines which were engrafted into the rat cerebellum to form neurons and glial cells. In other studies, murine neuroepithelial cells were immortalized with a retrovirus vector containing c-myc and were cultured with growth factors to form differentiated cell types similar to astrocytes and neurons (Barlett, et al., *Proc.Natl.Acad.Sci. USA,* 85:3255,1988).

Pioneering studies by Raff and colleagues (Raff, et al., Nature, 303:390, 1983) evidenced the existence of a bipotential glial progenitor cell in the rat optic nerve which, under the appropriate growth conditions, has the power to differentiate into oligodendrocytes or type II astrocytes. This progenitor cell, named O-2A, has come to represent a key bifurcation point in cell lineage and cellular differentiation in the CNS.

Oligodendrocytes are the myelin producing cells of the central nervous system. Death of oligodendrocytes appears to be causal in the demyelination seen in multiple sclerosis (Waxman, S. G., *New Engl J Med.,* 306:1529, 1982), or periventricular white matter injury thought to underlie spastic motor and cognitive deficits frequently seen in premature infants (Oka, et al., *J Neurosci.,* 13:1441, 1993). Oligodendrocytes appear to be terminally differentiated cells which do not undergo further cell division in vivo, and therefore have not been be cultured in vitro (Verity, et al., *J Neurochem.,* 60:577, 1993). Cultured oligodendrocyte precursors, therefore, offer a system by which the cellular and molecular mechanisms of demyelination might be studied in vitro.

The initial identification of a bipotential oligodendrocyte/type II astrocyte progenitor cell in newborn rat optic nerve (Raff, et al., supra) led to many studies on cells of this developmental lineage (Noble, M., *Recent Results in Cancer Research,* 135:67, 1994). Though some details of the O-2A model remain controversial, it is believed that O-2A cells are widely distributed throughout the mammalian brain, existing in both fetal and adult mammals (Wolswijk and Noble, *Development,* 105:387, 1989; Gonye, et al., *J Neurosci.,* 14:5365, 1994). While the rat cell line is useful for mammalian oligodendrocyte/astrocyte studies, species differences exist, and to date, no similar human cell lines have been developed.

Therapeutic grafting has particular promise in demyelinating disease such as multiple sclerosis. In the rat, oligodendrocyte progenitor cultures that have been grown and expanded in vitro can be engrafted back into the animal. Mice mutant for myelin production can serve as the recipients of these cells, and marked cells can be seen to migrate, engraft, differentiate and myelinate recipient nerve fibers (Espinosa de los Monteros, et al., *Dev. Neurosci.,* 14:98, 1992). Such observations support the prospects of the use of human oligodendrocyte progenitors in grafting, as a therapy in demyelinating disease, and perhaps following trauma to the CNS. In recent years the idea of grafting human tissue as a therapy for neurodegenerative disease has received increased attention (Bjorkland, *Nature*, 362:414, 1993). Transplantation approaches are limited by the availability of donor tissue. Certainly tissue cultured cells that can be expanded in vitro could circumvent the problems of tissue availability.

In view of the foregoing, there is a need for a long-term in vitro culture system which would allow large scale production and maintenance of a CNS cell population, and particularly a glial progenitor cell line, which will proliferate and can be passaged and subcultured over time. Such homogenous in vitro cell cultures will prove invaluable in studying cell populations, the interactions between these cells and the effects of various neuroactive compositions on these cells.

SUMMARY OF THE INVENTION

The present invention provides a pre-oligodendroglial stem cell line that is capable of indefinite growth and maintenance in vitro. These human oligodendroglial progenitor (HOP-1) cells are at least bipotential and can be induced to differentiate to produce astrocytes or oligodendrocytes. The pre-oligodendroglial stem cell of the invention is useful for transfer of an exogenous gene, such as a receptor or a ligand, and grafting into the central nervous system (CNS).

In a first embodiment, the invention provides a cell line having the characteristics of a pre-oligodendroglial stem cell which is essentially free of astrocyte and oligodendrocyte cell surface markers. The cells are essentially free of cell surface markers GFAP, GalC, O4, ganglioside $GD_3$ and A2B5, but bind to anti-vimentin antibody.

In another embodiment, the invention provides a method of producing an oligodendrocyte or an astrocyte. The invention also includes a method for identifying a composition which affects a pre-oligodendroglial stem cell which comprises incubating components comprising the composition and the pre-oligodendroglial stem cell wherein the incubating is carried out under conditions sufficient to allow the components to interact and measuring the effect on the pre-oligodendroglial stem cell caused by the composition. Such a method provides a means for valuable drug discovery. The HOP-1 cells of the invention are also useful for screening ligands or cell surface receptors.

BRIEF DESCRIPTION OF THE DRAWINGS

FIG. 2 shows a growth curve for HOP-1 cells.

DETAILED DESCRIPTION OF THE INVENTION

Figure 1A:
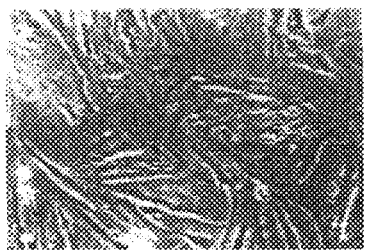
FIGS. 1A–1F show characterization of HOP-1 culture, before and after differentiation. Panels A & B show light field photographs. (A) Long term, primary culture of fetal human brain cells, without 'growth constraint'. (B) Growth constrained culture HOP-1. (C-F) Fluorescence photographs. (C) HOP-1 culture grown for one week at low density in the presence of serum, stained with anti-glial fibrillary acidic protein (GFAP), with a fluorescein-conjugated secondary antibody. (D) Undifferentiated HOP-1 stained with anti-vimentin, followed by a fluorescein-conjugated secondary antibody. (E & F) HF-0-2A seeded at low density, in serum-free media. (E) Stained with anti-O4, with a rhodamine-conjugated secondary antibody. (F) Stained with anti-galactocerebroside (GalC), followed by a fluorescein-conjugated secondary antibody.
Figure 1B:
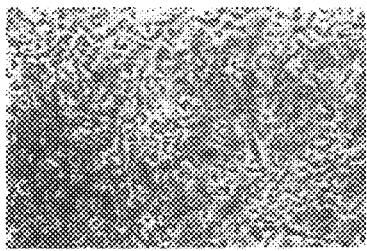
Figure 1C:
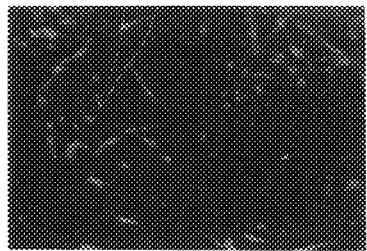
Figure 1D:
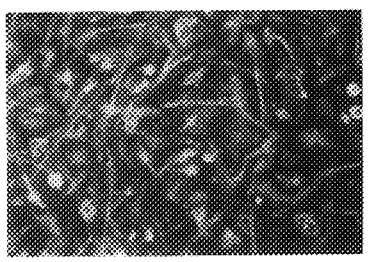
Figure 1E:
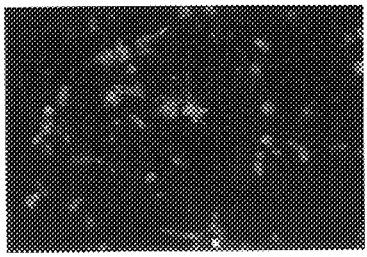
Figure 1F:
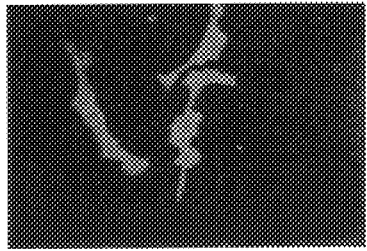

The present invention provides an in vitro method for producing an isolated glial cell population. These cells, termed "pre-oligodendroglial stem cells", are produced by utilizing methodology which comprises culturing a tissue containing glial cells at a high cell density in a basal media including serum and using a vessel which allows attachment of the cell. This method allows the generation of continuous, cell cultures from different regions of the brain, from both fetal and adult tissue, which are capable of indefinite proliferation and differentiation.

The invention also provides a method of identifying compositions which affect a pre-oligodendroglial stem cell, such as by inhibiting or stimulating the pre-oligodendroglial stem cell to proliferate or differentiate. An enriched population of pre-oligodendroglial stem cell cells produced by the method of the invention is also provided and can be further utilized for the treatment of a subject with a CNS cell disorder or alternatively, to screen for compositions which affect the pre-oligodendroglial stem cell.

As used herein, the term "pre-oligodendroglial stem cell" refers to a cell of the glial lineage which is "essentially free of", or stains negative for glial fibrillary acidic protein (GFAP) (astrocyte cytoskeletal marker), galactocerebroside (GalC) (oligodendrocyte marker), 04 (oligodendrocyte marker) ganglioside $GD_3$ and A2B5 (oligodendrocyte surface marker) and is essentially unresponsive to basic fibroblast growth factor (bFGF) and platelet derived growth factor (PDGF). In addition, the cells of the invention stain with anti-vimentin antibody, which is characteristic of immature cells of the CNS. The pre-oligodendroglial stem cells of the invention express the class of glutamate receptors called kainate receptors. Pre-oligodendroglial stem cells can be induced to express markers of terminal differentiation by splitting the cells to a low density. The term "low density" refers to culture of cells at a density of about $3.5 \times 10^5$ cells per 60 mm, or about $3.5 \times 10^5$ per 28 cm$^2$ or about $1.25 \times 10^4$ per cm$^2$. The term "high density" refers to culture of cells at a density approximately 10-fold higher than low density, e.g., $3.5 \times 10^6$ cells per 60 mm, or about $3.5 \times 10^6$ per 28 cm$^2$ or about $1.25 \times 10^5$ per cm$^2$. After culture at low density and in the absence of serum, pre-oligodendroglial stem cells express markers of oligodendrocytes (GalC, 04, ganglioside $GD_3$ and myelin basic protein). When split to low density in the presence of serum, such as about 10% serum, the majority of the cells stain positively for the astrocyte cytoskeletal marker, GFAP and appear to be astrocytic cells.

Assays for identification of high or low density cultures include actual counting of the cells with a hemocytometer, trypsin blue exclusion, and uptake of tritiated thymidine, for example. Labeling of nuclei or uptake of tritiated thymidine is most useful for determining cell proliferation and contact inhibition. These and other such methods are well known in the art.

Initial culture for isolation of a pre-oligodendroglial stem cell as described herein, requires dissociation of tissue from the CNS. After cells are dissociated and grown at high density, they are passaged at approximately 1:2 every 14 days. After a short period of time (approximately, 3 months) clones of cells appear which are capable of indefinite maintenance, growth, proliferation, and differentiation in vitro. Typically, a primary culture, one in which the tissue is removed from an animal, is placed in a culture vessel in appropriate fluid medium, and has a finite lifetime. In contrast, continuous cell lines proliferate and, thus, can be subcultured, i.e., passaged repeatedly into new culture vessels. Continuous cell lines can also be stored for long periods of time in a frozen state in the vapor phase of liquid nitrogen when a cryopreservative is present, e.g., 10% dimethylsulfoxide or glycerol. The pre-oligodendroglial stem cell of the invention can be maintained in long-term culture as a cell line closely resembling primary cultures, but without resort to oncogenic immortalization. Rather, the method of the invention establishes a continuous culture from a primary neural cell by utilizing a nutrient media which includes serum. This culture technique is novel in that no gene transfer or genetic manipulation is required and, as a consequence, the cells more closely resemble primary cultures.

There are hundreds of different types of cells of the nervous system, each with distinct properties. Each type of cell produces and responds to different combinations of neurotransmitters and neurotrophic factors. Cells of the nervous system do not divide in the adult brain, nor do they generally survive long in vitro. The method of the invention provides for the isolation and growth of pre-oligodendroglial stem cells, in vitro, which can be isolated from virtually any region of the brain and spinal cord. Either embryonic or adult tissue can be utilized for the development of pre-oligodendroglial stem cell lines. The tissue containing the cells of the invention, which is utilized for production of a pre-oligodendroglial stem cell, can be derived from any fetal or adult neural tissue, including tissue from the hippocampus, cerebellum, spinal cord, cortex (e.g., motor or somatosensory cortex), striatum, basal forebrain (cholinergic neurons), ventral mesencephalon (cells of the substantia nigra), and the locus ceruleus (neuroadrenaline cells of the central nervous system), and hypothalamus.

The liquid media for production of a pre-oligodendroglial stem cell of the invention is supplemented with serum, such as fetal calf serum, to support the growth and proliferation of a pre-oligodendroglial stem cell. Serum provides a variety of growth and trophic factors which are involved in the development and survival of the pre-oligodendroglial stem cell. These factors are often synthesized in the brain, have specific receptors, and influence the survival and function of cells. The specificity and selectivity of a growth or trophic factor are determined by its receptor. The specific neurotrophic factor which allows growth and proliferation of the pre-oligodendroglial stem cell in vitro will depend on the tissue origin of the pre-oligodendroglial stem cell. Preferably, the cells are cultured in the presence of serum from about 2% to 10%. Serum concentrations below 2% result in a decrease in cell growth. Most preferably the cells are cultured in about 10% serum.

The vessel utilized for production of a pre-oligodendroglial stem cell must provide a surface which allows attachment of the cell. Such vessels are also preferred for additional cell growth once the isolated pre-oligodendroglial stem cell culture has been produced. The surface used to enhance attachment of the cell can be the actual inner layer of the vessel, or more indirectly, the surface of a supplemental insert or membrane which resides within the vessel. Attachment may be accomplished by any means which allows the cell to grow as a monolayer on a vessel. Attachment enhancing surfaces can be produced directly, such as by advantageous selecting of appropriate plastic polymers for the vessel or, indirectly, as by treating the surface in the vessel by a secondary chemical treatment. Therefore, "attachment" refers to the ability of a cell to adhere to a surface in a tissue culture vessel, wherein the attachment promoting surface is in direct contact with cells, which otherwise would grow in a three-dimensional cellular aggregate in suspension. Attachment, or adherence, of a cell to the vessel surface allows it to be maintained indefinitely. In addition to interactions with soluble factors, most cells in vivo, including pre-oligodendroglial stem cells, are in contact with an extracellular matrix, a complex arrangement of interactive protein and polysaccharide molecules which are secreted locally and assemble into an intricate network in the spaces between cells. Therefore, the addition of an extracellular matrix protein to the surface of the culture vessel forms an insoluble matrix which allows neural cells in culture to adhere in a manner which closely corresponds to the in vivo extracellular matrix The pre-oligodendroglial stem cell of the invention can be preferably produced by coating the surface of a vessel, such as a tissue culture dish or flask, with a polybasic amino acid composition to allow initial attachment. Such compositions are well known in the art and include polyomithine and polylysine. Most preferably, the polybasic amino acid of the invention is polyornithine. Additionally, the surface of the vessel may be coated with a known extracellular matrix protein composition to enhance the pre-oligodendroglial stem cell's ability to grow and form processes on the substrate. Such compositions include laminin, collagen and fibronectin. Other extracellular matrix proteins that can be used in conjunction with a polybasic amino acid will be apparent to one of skill in the art.

The pre-oligodendroglial stem cell of the invention is useful as a screening tool for neuropharmacological compounds which affect a biological function of the pre-oligodendroglial stem cell. Thus, in another embodiment, the invention provides a method for identifying a composition which affects a pre-oligodendroglial stem cell comprising incubating the components, which include the composition to be tested and the pre-oligodendroglial stem cell, under conditions sufficient to allow the components to interact, then subsequently measuring the effect the composition on the pre-oligodendroglial stem cell. The observed effect on the pre-oligodendroglial stem cell may be either inhibitory or stimulatory. For example, a neuroactive compound which mimics a neurotransmitter or binds to a receptor and exhibits either an antagonistic or agonist effect, thereby inhibiting or stimulating a biological response in the pre-oligodendroglial stem cell, can be identified using the method of the invention. The occurrence of a biological response can be monitored using standard techniques known to those skilled in the art. For example, inhibition or stimulation of a biological response may be identified by the level of expression of certain genes in the pre-oligodendroglial stem cell. Such genes may include early response genes such as fos, myc or jun (Greenberg, M. and Ziff, E. *Nature,* 311:433, 1984; eds. Burck, et al., in *Oncogenes,* 1988, Springer-Verlag, New York.). Other genes, including those which encode cell surface markers can also be used as indicators of the effects neuropharmacological compounds on the pre-oligodendroglial stem cells of the invention. Methods for measurement of such effects include Northern blot analysis of RNA (transcription), SDS-PAGE analysis of protein (translation), [$^3$H]-thymidine uptake (DNA synthesis) and antibody reactivity (both intracellular and extracellular). Other commonly used methods will be apparent to those of skill in the art. The method of the invention is useful for identification of compositions which are useful for inducing differentiation of the pre-oligodendroglial cells of the invention toward the astrocytic or the oligodendrocytic pathway.

Neuroactive drugs which act similarly to those already known to affect neuronal or other cells of the CNS can thus be identified. For example, new drugs that alleviate anxiety, analogously to Valium, which augment or stimulate the action of the important inhibitory transmitter gamma-aminobutyric acid (GABA), can be identified. Antidepressants, such as Prozac, enhance the action of serotonin, an indoleamine with a wide variety of functions. Other drugs can be readily identified using the pre-oligodendroglial stem cells according to the method of the invention. Other examples include psychoactive compounds. For example, cocaine facilitates the action of dopamine, whereas certain antipsychotics antagonize or inhibit this catecholamine. Another example is nicotine which activates the acetylcholine receptors which are distributed throughout the cerebral cortex. Therefore, by using pre-oligodendroglial stem cells derived from tissue from the appropriate regions of the brain, drugs and trophic factors which bind various receptors can be identified using the method of the invention.

As described above, long term growth and maintenance of a pre-oligodendroglial stem cell can be accomplished without the use of oncogenic intervention. However, if desired the pre-oligodendroglial stem cell of the invention may be immortalized to maintain the cell at a defined developmental stage. The present techniques for immortalization typically involve the transfection of an oncogene to the cell, therefore, immortalization of a pre-oligodendroglial stem cell can be achieved by introduction of at least one oncogene to the pre-oligodendroglial stem cell. Transfection of the oncogene can be accomplished by several conventional methods well known to those skilled in the art, including using recombinant retroviruses, chemical, or physical methods. Recombinant retrovirus transfer is the preferred method of the invention for immortalization of pre-oligodendroglial stem cells.

The pre-oligodendroglial stem cell can be immortalized with a particular oncogene by such methods of transfection as calcium phosphate co-precipitation, conventional mechanical procedures such as microinjection, insertion of a plasmid encased in liposomes, or by use of viral vectors. For example, one method is to use a eukaryotic viral vector, such as simian virus 40 (SV40) or bovine papilloma virus, to transiently infect or transform the pre-oligodendroglial stem cell (*Eukaryotic Viral Vectors,* Cold Spring Harbor Laboratory, Gluzman ed., 1982).

Various viral vectors which can be utilized for immortalization as taught herein include adenovirus, adeno-associated virus, herpes virus, vaccinia, and preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), gibbon ape leukemia virus (GaLV) and Rous Sarcoma Virus (RSV). A number of additional retroviral vectors can incorporate multiple genes. All of these vectors can transfer or incorporate a gene for a selectable marker so that transduced cells can be identified and generated.

Since recombinant retroviruses are defective, they require assistance in order to produce infectious vector particles. This assistance can be provided, for example, by using helper cell lines that contain plasmids encoding all of the structural genes of the retrovirus (gag, env, and pol genes) under the control of regulatory sequences within the long terminal repeat (LTR). These plasmids are missing a nucleotide sequence which enables the packaging mechanism to recognize an RNA transcript for encapsidation. Helper cell lines which have deletions of the packaging signal include, but are not limited to Ψ2, PA3 17, PA12, CRIP, CRP-4 and CRE, for example. These cell lines produce empty virions, since no genome is packaged. If a retroviral vector is introduced into such cells in which the packaging signal is intact, but the structural genes are replaced by other genes of interest, the vector can be packaged and vector virion produced. The vector virions produced by this method can then be used to infect a tissue cell line, such as NIH 3T3 cells, to produce large quantities of chimeric retroviral virions.

Herpes virus-based vectors may also be used to transfer genes into a pre-oligodendroglial stem cell. Since herpes viruses are capable of establishing a latent infection and an apparently non-pathogenic relationship with some neural cells, such vector based on HSV-1, for example, may be used. Similarly, it should be possible to take advantage other human and animal viruses that infect cells of the CNS efficiently, such as rabies virus, measles, and other paramyxoviruses and even the human immunodeficiency retrovirus (HIV), to develop useful delivery and expression vectors.

When a recombinant retrovirus is engineered to contain an immortalizing oncogene, the oncogene can be any one of those known to immortalize. For example, such commonly used immortalizing genes include genes of the myc family (both c-myc and v-myc) (Bartlett, et al., *Proc.Natl.Acad.Sci. USA* 85:3255, 1988), adenovirus genes (E1a 12s and E1a 13s) (Ruley, et al., *Nature* 304:602, 1983), the polyoma large T antigen and SV40 large T antigen (Frederiksen, et al., *Neuron* 1:439, 1988). Preferably, the oncogene used to immortalize the pre-oligodendroglial stem cell of the invention is v-myc. Other genes, for example other nuclear oncogenes, that immortalize a cell but may require a second gene for complete transformation, will be known to those of skill in the art. In addition, the cells can be infected with a virus, such as HPV E7 (Human Papilloma Virus, Barbosa and Schlegel, *Oncogene,* 4:1529, 1989), for immortalization of the cell line. The same transfection methods described above for immortalization of a pre-oligodendroglial stem cell can be utilized to transfer other exogenous genes to the pre-oligodendroglial stem cell of the invention. An "exogenous gene" refers to regulatory or structural genetic material from outside the pre-oligodendroglial stem cell which is introduced into the pre-oligodendroglial stem cell. An example of a desirable exogenous gene which would be useful for the method of identifying neuropharmacological compounds is a gene for a receptor molecule. For example, such neuronal receptors include the receptor which binds dopamine, GABA, adrenaline, noradrenaline, serotonin, glutamate, acetylcholine and various other neuropeptides. Transfer and expression of a particular receptor in a pre-oligodendroglial stem cell of specific neural origin, would allow identification of neuroactive drugs and trophic factors which may be useful for the treatment of diseases involving that pre-oligodendroglial stem cell type and that receptor. For example, a neuroactive compound which mimics a neurotransmitter and binds to a receptor and exhibits either an antagonistic or agonist effect, thereby inhibiting or stimulating a response in the pre-oligodendroglial stem cell, can be identified using the method of the invention.

The invention also provides a cellular composition comprising an enriched population of pre-oligodendroglial stem cell cells. The composition preferably contains a majority of or at least about 90% pre-oligodendroglial stem cells. The pre-oligodendroglial stem cells are derived from any CNS neural tissue such as from any region of the brain, as described above, or from the spinal cord. The pre-oligodendroglial stem cell may be further immortalized with an oncogene, or it may contain an exogenous gene encoding a receptor or a ligand for a receptor. An exemplary pre-oligodendroglial stem cell line as described herein has been deposited pursuant to the Budapest Treaty requirements with the American Type Culture Collection (ATCC), Rockville, Md.

The present invention also provides a method of treating a subject with a cell disorder of the CNS which comprises administering to the subject a therapeutically effective amount of the pre-oligodendroglial stem cell of the invention. "Therapeutically effective" as used herein, refers to that amount of pre-oligodendroglial stem cell that is of sufficient quantity to ameliorate the cause of the CNS disorder. "Ameliorate" refers to a lessening of the detrimental effect of the CNS disorder in the patient receiving the therapy. The subject of the invention is preferably a human, however, it can be envisioned that any animal with a CNS disorder can be treated with the pre-oligodendroglial stem cell of the invention. Preferably, the pre-oligodendroglial stem cell is derived from CNS tissue of the same species as the species of the subject receiving therapy.

The method of treating a subject with a CNS disorder entails intracerebral grafting of pre-oligodendroglial stem cells, or oligodendrocytes or astrocytes which have been induced to differentiate from the pre-oligodendroglial cells, to the region of the CNS having the disorder. Where necessary, the pre-oligodendroglial stem cell, oligodendrocyte or astrocyte, can be genetically engineered to contain an exogenous gene. The disorder may be from either disease or trauma (injury). Pre-oligodendroglial stem cell transplantation, or "grafting" involves transplantation of cells into the central nervous system or into the ventricular cavities or subdurally onto the surface of a host brain. Such methods for grafting will be known to those skilled in the art and are described in *Neural Grafting in the Mammalian CNS,* Bjorklund and Stenevi, eds., (1985), incorporated by reference herein. Procedures include intraparenchymal transplantation, (i.e., within the host brain) achieved by injection or deposition of tissue within the host brain so as to be apposed to the brain parenchyma at the time of transplantation.

Administration of the pre-oligodendroglial stem cells of the invention into selected regions of the recipient subject's brain may be made by drilling a hole and piercing the dura to permit the needle of a microsyringe to be inserted. The pre-oligodendroglial stem cells can alternatively be injected intrathecally into the spinal cord region. The pre-oligodendroglial stem cell preparation of the invention permits grafting of pre-oligodendroglial stem cells to any predetermined site in the brain or spinal cord, and allows multiple grafting simultaneously in several different sites using the same cell suspension and permits mixtures of cells from different anatomical regions. For example, the pre-oligodendroglial stem cells or differentiated cells (oligodendrocytes) can be grafted into the CNS of a subject with multiple sclerosis, wherein the subject's oligodendrocytes have died. The present invention provides a method for transplanting various neural tissues, by providing previously unavailable proliferating pre-oligodendroglial stem cells and a culture system for production of these pre-oligodendroglial stem cells in order to grow a sufficient number of cells for in vitro gene transfer followed by in vivo implantation.

The pre-oligodendroglial stem cell used for treatment of a CNS disorder may optionally contain an exogenous gene, for example, an oncogene, a gene which encodes a receptor, or a gene which encodes a ligand. Such receptors include receptors which respond to dopamine, GABA, adrenaline, noradrenaline, serotonin, glutamate, acetylcholine and other neuropeptides, as described above. Examples of ligands which may provide a therapeutic effect in a CNS disorder include dopamine, adrenaline, noradrenaline, acetylcholine, gamma-aminobutyric acid and serotonin. The diffusion and uptake of a required ligand after secretion by a donor pre-oligodendroglial stem cell would be beneficial in a disorder where the subject's neural cell is defective in the production of such a gene product. A pre-oligodendroglial stem cell genetically modified to secrete a neurotrophic factor, such as nerve growth factor, (NGF), might be used to prevent degeneration of cholinergic neurons that might otherwise die without treatment. Alternatively, pre-oligodendroglial stem cells to be grafted into a subject with a disorder of the basal ganglia, such as Parkinson's disease, can be modified to contain an exogenous gene encoding L-DOPA, the precursor to dopamine. Parkinson's disease is characterized by a loss of dopamine neurons in the substantia-nigra of the midbrain, which have the basal ganglia as their major target organ. Alternatively, pre-oligodendroglial stem cells derived from substantia-nigra CNS cells which produce dopamine could be introduced into a Parkinson's patient brain to provide cells which "naturally" produce dopamine.

Other CNS disorders that can be treated similarly by the method of the invention include Alzheimer's disease, Huntington's disease, CNS damage due to stroke, and damage in the spinal cord. Alzheimer's disease is characterized by degeneration of the cholinergic neurons of the basal forebrain. The neurotransmitter for these neurons is acetylcholine, which is necessary for their survival. Engraftment of cholinergic pre-oligodendroglial stem cells, or pre-oligodendroglial stem cells containing an exogenous gene for a factor which would promote survival of these neurons can be accomplished by the method of the invention, as described. Following a stroke, there is selective loss of cells in the CA1 of the hippocampus as well as cortical cell loss which may underlie cognitive function and memory loss in these patients. Once identified, molecules responsible for CA1 cell death can be inhibited by the methods of this invention. For example, antisense sequences, or a gene encoding an antagonist can be transferred to a pre-oligodendroglial stem cell and implanted into the hippocampal region of the brain.

Antisense sequences or antagonists may also be transferred to a pre-oligodendroglial stem cell for grafting in an area of a malignant astrocytoma or glioblastoma. For example, at least four oncogenes (sis, myc, src, and n-myc) have been identified in cell lines from primary brain tumors and these cells also overexpressed the PDGF and EGF receptors. Therefore, the cells of the invention may be manipulated to produce a c-myc antisense, for example, and such cells can be implanted in the region of the tumor.

The method of treating a subject with a CNS disorder also contemplates the grafting of pre-oligodendroglial stem cells in combination with other therapeutic procedures useful in the treatment of disorders of the CNS. For example, the pre-oligodendroglial stem cells can be co-administered with agents such as growth factors, gangliosides, antibiotics, neurotransmitters, neurohormones, toxins, neurite promoting molecules and antimetabolites and precursors of these molecules such as the precursor of dopamine, L-DOPA.

The following examples are intended to illustrate but not limit the invention. While they are typical of those that might be used, other procedures known to those skilled in the art may alternatively be used.

EXAMPLES

The following Examples describe a novel glial cell line which has the characteristics of an early pre-oligodendroglial stem cell. Such cells are at least bipotential and capable of differentiating into astrocytes or oligodendrocytes.

EXAMPLE 1

Materials and Methods

1. Tissue Dissociation

Human fetal brain tissue was obtained from 10–14 week abortions (Advanced Biosciences Resources, Alameda, Calif.). This tissue was treated with trypsin at 37° C. for 15 min. before being triturated through a fire-polished Pasteur pipette to yield a suspension consisting predominantly of single cells. Cells were plated into Ham's DMEM/F12 with 10% fetal calf serum. Cultures were initially plated onto polyornithine/laminin coated plastic.

2. Growth Constraint Selection

'Growth constraint selection' has been described with reference to conditions giving rise to spontaneous immortalization of rodent fibroblast cells in culture (Chow, et al., *Proc. Natl. Acad Sci., USA*, 91:599, 1994). In brief, the approach is based on the idea that immortal cells have a growth advantage over non-immortal cells in culture. By 'constraining' the culture to hasten senescence of primary cells, pre-existing immortal cells will dominate and eventually overtake the culture.

Cells were dissociated and plated at high density on polyornithine/laminin, in Hams/F12 supplemented with 10% fetal calf serum. Cells were passaged on a '14t1/2' schedule, being split 1:2 every 14 days. After about 3 months, clones of cells began to appear, growing atop the senescent flat cells. These new cells were immortal progenitors and, over continuous passage (>6 months) completely overtook the culture. At this point, the population was phenotypically homogeneous, and could be grown on standard tissue culture plastic. The doubling time of this culture was 18 hours. After this point, the culture was stable since no changes in growth rate or phenotypic characteristics could be seen over a period of several months. This technique reproducibly gave rise to the same types of cells - pre-oligodendroglial stem cells or astrocyte/oligodendrocyte progenitors.

3. Cellular Differentiation

Cultures were differentiated using conditions similar to those noted to be optimal for the rat O-2A cells (Raff, et al., supra), with some modifications. It was initially noted that cultures seeded at low density spontaneously differentiated to GFAP+astrocyte-like cells after two to three days in culture. GalC+oligodendrocyte-like cells could be generated by splitting the cells at low density into media containing 10% fetal calf serum. As soon as the cells attached to the plastic, the media was changed to DMEM/F12 without serum. GalC+cells appeared transiently over the next few days.

4. Immunocytochemistry

Antibodies were obtained from the following sources: anti-vimentin, monoclonal: Boehringer Mannheim; anti-A2B5, monoclonal: Boehringer Mannheim; anti-GalC, monoclonal: Boehringer Mannheim; anti-GFAP, polyclonal: Chemicon; anti-O4, monoclonal: Boehringer Mannheim; anti-MBP, monoclonal: Boehringer Mannheim; anti-CNP, monoclonal: Chemicon.

For immunohistochemistry, cells were grown on polyornithine/laminin coated glass cover slips. For intracellular antigens (GFAP, vimentin) cells were fixed with 2% paraformaldehyde in PBS, pH 7.2 for 20 min, and permeabilized in 2% Triton X-100 and 0.2% normal goat serum in PBS for 30 min. For surface antigens, primary antibodies were applied to unfixed cells. Dilutions of primary antibody/ antisera were prepared in PBS plus 2% normal goat serum, and applied to cells for one hour. Cells were washed three times in PBS. Secondary antibodies (conjugated to either fluorescein or rhodamine) were applied to the cells at the appropriate dilution in PBS, 2% goat serum. Secondary antibody for intracellular epitopes were prepared in solution together with 2% Triton X100. Care was taken to minimize the exposure of fluorescent tagged antibodies to light. Secondary antibody was applied for from one hour. Cells were then washed three times with PBS. At this point unfixed cells (surface antigens) were fixed in 2% paraformaldehyde for 20 min. Fixed cells on coverslips were inverted onto Vectashield (Vector Laboratories) on microscope slides.

5. Transfection

Calcium phosphate transfection was carried by the method of Chen and Okayama (Chen and Okayama, *Mol. Cell Biol.*, 7:2745, 1987).

6. Growth Curves

Growth curves were carried out by direct counting of trypan blue-excluded cells. MTS calorimetric assays were also used in the generation of growth curves.

7. MTS assays

MTS assays were carried out using the Promega MTS assay system.

8. Growth in Soft Agar

Anchorage independence is considered to be one measure of transformed phenotype. Soft agar analysis was performed according to published protocol (Rouget, et al., *Neuronal Cell Lines: A Practical Approach*, IRL Press at Oxford Univ. Press, Oxford, 1992).

9. Karyotype Analysis.

Aneuploid karayotype is also indicative of transformation. Metaphase chromosome analysis was carried out according to published protocol (Rouget, et al., supra). 20 separate karyotype analyses showed diploid cells in each spread.

EXAMPLE 2

PRE-OLIGODENDROGLIAL STEM CELLS DIFFERENTIATE INTO ASTROCYTES OR OLIGODENDROCYTES

When cultured at high density, HOP-1 (the exemplary oligodendroglial progenitor stem cells of the invention) cultures did not express antigens characteristic of neurons, astrocytes or oligodendrocytes. When split to low density, HOP-1 cells expressed antigens characteristic of terminal differentiation. These markers differ if the cells are grown in serum free media, verses media containing serum (see FIG. 1). FIG. 1 shows characterization of HOP-1 culture, before and after differentiation. Panels A & B show light field photographs. Panel (A) shows long term, primary culture of fetal human brain cells, without 'growth constraint'. Panel (B) shows growth constrained culture of HOP-1. Panels (C-F) show fluorescence photographs. In panel (C) HOP-1 culture grown for one week at low density in the presence of serum, stained with anti-glial fibrillary acidic protein (GFAP), with a fluorescein-conjugated secondary antibody. In panel (D), undifferentiated HOP-1 stained with anti-vimentin, followed by a fluorescein-conjugated secondary antibody. Panels E & F show HOP-1 seeded at low density, in serum-free media. In panel (E), cells stained with anti-04, with a rhodamine-conjugated secondary antibody. Panel (F) shows cells stained with anti-galactocerebroside (GalC), followed by a fluorescein-conjugated secondary antibody.

HOP-1 was characterized immunohistochemically as follows:

TABLE 1

IMMUNOHISTOCHEMICAL PROFILE OF HOP-1

| | Undifferentiated | Differentiated (+serum) | Differentiated (−serum) |
|---|---|---|---|
| GFAP (astrocytes) | − | + | − |
| GalC (oligo-dendrocytes) | − | − | + |
| O4 (oligo-dendrocytes) | − | − | + |
| A2B5 (progenitors) | − | − | − |
| Vimentin (progenitors) | + | + | + |
| GD$_3$ | − | + | + |

− = unreactive with antibody
+ = reactive with antibody

These results indicated that HOP-1 is an astrocyte/oligodendrocyte progenitor cell, similar to the O-2A cell characterized in rat by Raff and colleagues (Raff, et al., supra), and others. The rat O-2A cell is a bipotential oligodendrocyte/astrocyte progenitor cell found throughout CNS white matter (Gonye, et al., supra) in both perinatal and adult rat (Wolswijk and Noble, supra). Under the appropriate in vitro culture conditions this bipotential cell differentiates into oligodendrocytes or type II astrocytes. A further distinction has been made between rat O-2A cells derived from fetal animals verses those seen in the adult (Wolswijk and Noble 1989). Rat O-2A$^{perinatal}$ cells are positive for the A2B5 antigen (a progenitor marker), have a doubling time of 18 hours, and are responsive to bFGF and PDGF. Rat O-2A$^{adult}$ cells are A2B5 negative, have a doubling time of 72 hours, and do not recognize bFGF or PDGF as mitogens (Armstrong, et al., J Neurosci., 12:1538, 1990). Human cultures share some properties with the rat perinatal cells (discussed further below). Rat O-2A$^{perinatal}$ cells express the ganglioside GD$_3$ (Hardy and Reynolds, Development, 111:1061, 1991). HOP-1 cells are GD$_3$ negative until the cells differentiate. Therefore, the differences between HOP-1 and rat O-2A cultures may be due to differences between developmental stages of the CNS. While not wanting to be bound by a particular theory, it is believed that HOP-1 is an earlier stage cell line.

TABLE 2

COMPARISON OF HOP-1 AND RAT O-2A CELLS

| | rat O-2A perinatal | rat O-2A adult | HOP-1 |
|---|---|---|---|
| A2B5 | + | − | − |
| bFGF/PDGF | + | + | − |

The results in Table 2 show that the human cell line described herein does not express A2B5 antigen and is unresponsive to PDGF and bFGF. Therefore, these human pre-oligodendroglial cells are distinct from the previously described rat oligodendrocyte progenitor cells. In addition, HOP-1 cells differentiate to astrocytes (GFAP+cells) in vitro, however, the percentage of cells expressing GalC is significantly less (~5%) than seen for rat-O-2A. Therefore, it is likely that HOP-1 cells utilize the astrocyte lineage as the "default" pathway in vitro.

EXAMPLE 3

CHARACTERIZATION OF PRE-OLIGODENDROGLIAL STEM CELLS

Like the rat cell line CG-4, HOP-1 is a perpetuated culture of oligodendrocyte progenitors. HOP-1 cultures have additional features of immortality, however. HOP-1 cells will grow in low (1%) serum and retain the property of contact inhibition. FIG. 2 shows a typical growth curve for these pre-oligodendroglial stem cells. One culture of HOP-1 cells has gone through more than 60 population doublings, and has been in culture for more than 8 months without displaying any signs of senescence. HOP-1 cells are diploid and do not grow in soft agar. Taken together, these data evidence that HOP-1 are an immortal, non-transformed cell culture.

The growth factors PDGF and bFGF are mitogenic for the rat O-2A cell, and can be used to generate the perpetuated O-2A cell line CG-4 (Louis, et al., J Neuro. Res., 31:193, 1992). In contrast, HOP-1 grows as a perpetuated line in the presence of 10% fetal calf serum, and does not recognize bFGF or PDGF as mitogens. These results are consistent with observations indicating the independence of human oligodendrocytes from these growth factors.

EXAMPLE 4

APOPTOSIS IN PRE-OLIGODENDROGLIAL STEM CELLS

TNF-α and IL-1β are inflammatory cytokines, and have been implicated in the destruction of oligodendrocytes in multiple sclerosis (Hofman, et al., J Exp. Med, 170:607, 1989; Selmaj, et al., J Immunol., 147:1522, 1991). Apoptosis can be initiated by TNF-α in the rat O-2A cell, and this effect can be blocked by CNTF (Louis, et al., supra). Therefore, studies were performed to determine whether TNF-α will also initiate apoptosis in HOP-1 cells.

FIG. 3 shows MTS assays of HOP-1 cells in 96-well plate format. On day 1, cells were plated in serial dilutions in a 96 well plate. Cytokines (100 ng/ml) were added on days 2 and 5, in serum containing media. On day 8, MTS absorbance was determined. MTS absorbance (Y value) directly reflects the number of viable cells.

Figure 3B:
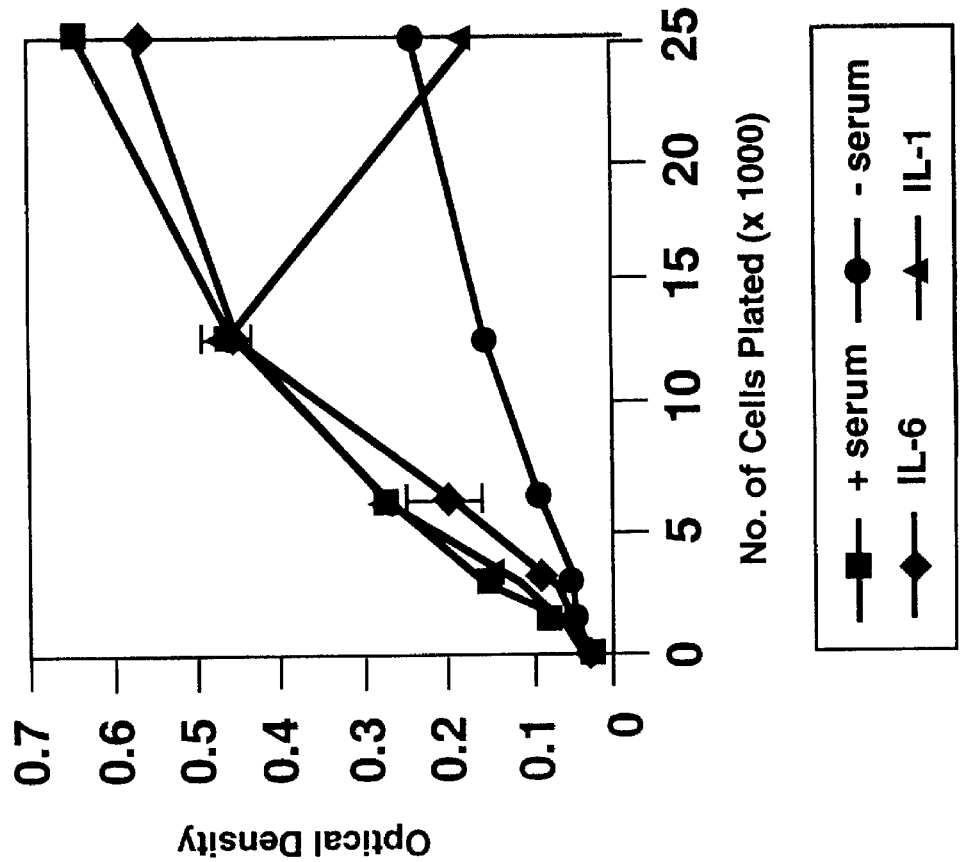
FIG. 3 shows MTS assays of HOP-1 in 96-well plate format. On day 1, cells were plated in serial dilutions in a 96 well plate. Cytokines (100 ng/ml) were added on days 2 and 5, in serum containing media. On day 8, MTS absorbance was determined. MTS absorbance (Y value) directly reflects the number of viable cells. Panel A shows that TNF-α decreases the numbers of viable cells over serum containing media. Panel B shows that, versus serum containing media, IL-1β but not IL-6 promotes cell death in HOP-1.
Figure 3A:
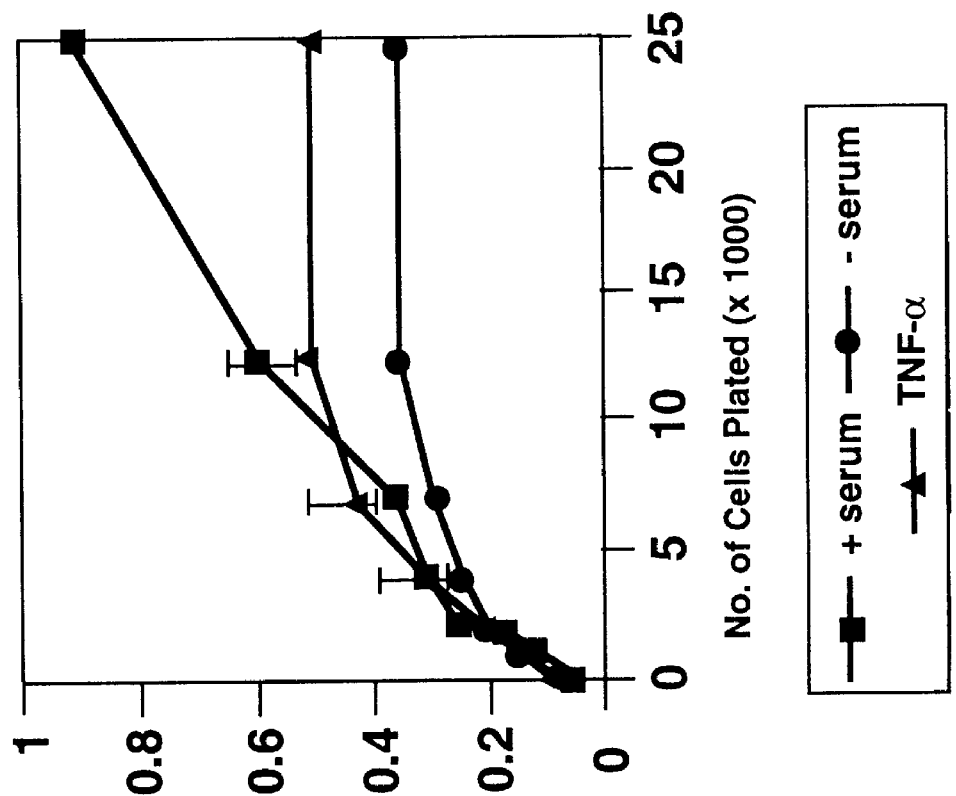

The results in FIG. 3A show that TNF-α decreases the numbers of viable cells over serum containing media. Hoechst staining confirms that TNF-α promotes apoptotic cell death in HOP-1, just as it does in rat O-2A (CG-4, Louis, et al., supra). FIG. 3B shows that, verses serum containing media, IL-1β but not IL-6 promotes cell death in HOP-1 cells. Again, Hoechst staining confirmed that the reduction in MTS absorbance values was due to apoptosis. In each case, cytokines were more destructive to cells plated at the higher densities.

EXAMPLE 5

GENE TRANSFER IN PRE-OLIGODENDROGLIAL STEM CELLS

With an interest in gene therapy or grafting, it may be desirable to genetically engineer the grafted cell so that it will be able to evade further damage from the immune system or express a particular gene of interest. In order to genetically engineer cells, foreign genes can be introduced by infection, using retroviral vectors (Miller, et al., *Methods in Enzymology*, 217:581, 1993), or by transfection (Chen and Okayama, supra). Using standard gene transfer techniques, studies showed that HOP-1 cultures are readily infectable by amphotropic MMLV and readily express β-galactosidase carried by the MMLV (as determined by the method of Miller, et al. *Methods of Enz.*, 217:581, 1993) They are also transfectable at high efficiency (>10% of the cells) by standard calcium phosphate technique.

EXAMPLE 6

GLUTAMATE RECEPTORS

Figure 4:
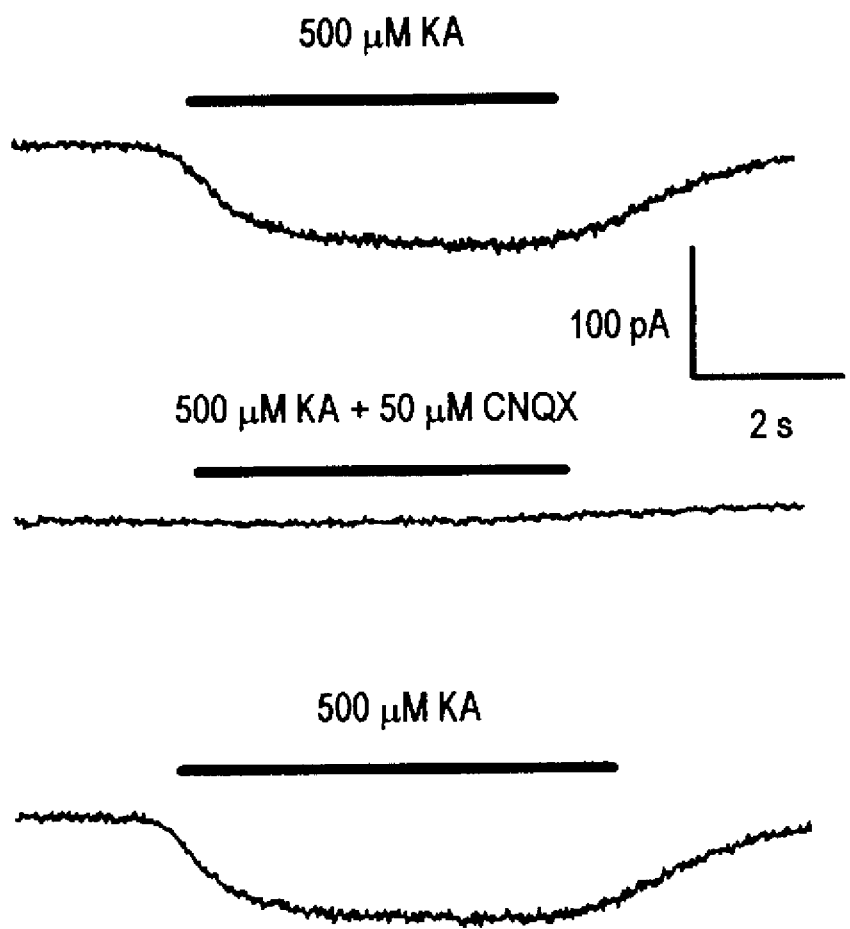
FIG. 4 shows voltage and ligand gated currents for kainate, sodium, calcium, NMDA and glycine, and GABA.

Glutamate is a neurotransmitter in the brain whose action is mediated by receptors, only a few of which have been seen on cultured cells. They are a very good target for development of pharmaceuticals. The receptor class is subclassified by pharmacological ligand specificity. On class of glutamate receptors are the kainate receptors. In order to determine whether or not glutamate receptors were present on HOP-1 cells a voltage and ligand-gated current experiment was performed (FIG. 4).

Whole-cell patch-clamp recordings were made (Hamill, et al., *Pflugers Arch.*, 391:85, 1981) from HOP-1 cells in an external bathing solution of 150 mM NaCl, 3 mM KCl, 1.0 mM $CaCl_2$, 10 mM Hepes (pH 7.3). Pipettes (resistance 3–15 MΩ) were filled with a solution that contained 110 mM CsF, 30 mM CsCl, 5 mM EGTA, 5 mM Hepes, 4 mM NaCl, 0.5 mM $CaCl_2$ (pH 7.2). Drugs were applied to the cells via a multipanelled array of pipettes. Co-applications of the competitive non-NMDA receptor antagonist 6-cyano-7-nitroquinoxaline-2,3-dione (5 $\mu$M;CNQX) with 500 $\mu$M kainate reduced steady state current responses in HOP-1 cells as expected if these currents arise from agonist-gated glutamate receptors. The results are shown in TABLE 3, and indicate the presence of kainate receptors.

TABLE 3

VOLTAGE AND LIGAND-GATED CURRENTS

| Type of Current | | |
|---|---|---|
| Sodium | Present | 0/5 cells |
| Calcium | Present | 3/4 cells |
| | Range of I (pA) | 96–126 |
| NMDA + Glycine | Present | 0/9 cells |
| Kainate | Present | 4/10 cells |
| | Range of I (pA) | 76–129 |
| | Desensitization | 0/4 cells |

TABLE 3-continued

VOLTAGE AND LIGAND-GATED CURRENTS

| Type of Current | | |
|---|---|---|
| GABA | Present | 0/10 cells |

In addition, using polyclonal and monoclonal antisera for the glutamate receptor subunits, it was confirmed that HOP-1 cells possess glutamate receptors (TABLE 4).

TABLE 4

| HUMAN HOP-1 | |
|---|---|
| polyclonal antisera | |
| GluR 1 | ++ |
| GluR 2/3 | ++ |
| GluR 4 | ++ |
| monoclonal antibody | |
| GluR 2/4 | ++ |
| GluR 5/6/7 | ++ |
| #RT-PCR analysis of members of the kainate receptor family expressed by HOP-1 indicate the following: | |
| GluR 1 | + |
| GluR 2 | − |
| GluR 3 | + |
| RAT CG-4* | |
| GluR 1 | − |
| GluR 2 | + |
| GluR 3 | + |
| GluR 4 | + |
| GluR 5 | − |
| GluR 6 | + |
| GluR 7 | + |
| KA1 | + |
| KA2 | + |

*Puchalski, et al., Neuron, 13:1–20, 1994. Selective RNA Editing and Subunit Assembly of Native Glutamate Receptors.
In HOP-1 cells, GluR 1 is present and GluR 2 is absent, in contrast to CG-4, where GluR 1 is absent, and GluR 2 is present.
− = unreactive with antisera and by RT-PCR
+ = reactive with antisera and by RT-PCR The results in Table 4 indicate that all of the cells in the culture stained positively for each glutamate (kainate/NMDA) receptor subunit. These results show that the culture is homogeneous and in contrast to rat-O2A cells, the HOP-1 cells stain positive for GluR1.

SUMMARY

The rat oligodendrocyte progenitor (O-2A) cell can be propagated in vitro through the use of the exogenous growth factors bFGF and PDGF. Such an approach has not been successful for the propagation of human oligodendrocyte progenitor cells, which appear to be refractory to these growth factors as shown herein. For this reason, established, pure cultures of human oligodendrocyte progenitors have not yet been reported. The present invention describes a technique of long-term culture which, when employed using primary dissociations of human fetal brain tissue, reproducibly gives rise to pure cultures of human oligodendrocyte progenitors. These cultures have been termed 'human oligodendrocyte progenitor cells', or HOP-1 cells. HOP-1 cells are derived from fetal tissue. These cells are not the human homologue of the rat $O2A^{perinatal}$ progenitor cell as shown from the various differences in cell markers. In fact, it appears that the cells described herein are an earlier progenitor stem cell.

HOP-1 cells are maintained in an undifferentiated state by culturing them at a very high density. Undifferentiated HOP-1 cells express the cytoskeletal protein vimentin, and do not stain for glial fibrillary acidic protein (GFAP) or galacto-cerebroside (GalC). Unlike the rat oligodendrocyte progenitor O-2A, HOP-1 cells are negative for the surface marker A2B5. HOP-1 progenitor cells can be induced to express markers of terminal differentiation by splitting them to low density. In the absence of serum, HOP-1 cells express markers of oligodendrocytes. Cells expressing the oligodendrocyte markers GalC, O4, vimentin, and myelin basic protein are described herein. When split to low density in the presence of serum that the majority of the cells stain positively for the astrocyte cytoskeletal marker, GFAP.

Rat O-2A cells can be perpetuated using neuroblastoma conditioned media, or by adding the exogenous growth factors PDGF and bFGF to the media (Louis et al. 1992). In this way O-2A cultures have been expanded and used in routine experimentation (Louis et al. 1992; Louis et al. 1993). Human O-2A-like cells are not responsive to PDGF or bFGF, however, and pure cultures of human progenitors have not been forthcoming. HOP-1 cells described here represent a perpetuated culture which does not require specially conditioned media or the addition of exogenous growth factors for their maintenance. When analyzed by BrDu incorporation assay in serum-free conditions, HOP-1 cells do not recognize either bFGF or PDGF as mitogens. As the growth rate of HOP-1 cells deceases following a change of the media, it would appear that these cells may condition their own media.

HOP-1 cultures appear to be immortal. HOP-1 cells grow in low (1%) serum. The culture maintains the property of contact inhibition. One population of HOP-1 cells has been in culture for greater than 8 months, and has surpassed 60 population doublings, without showing any signs of senescence. As of passage 12, HOP-1 cells are of normal karyotype, and do not form colonies in soft agar. Taken together, these features argue that HOP-1 cells are an immortal but not transformed cell culture. Multiple sclerosis is believed to be an autoimmune condition, which results in demyelination of nerve fibers by destruction of oligodendrocytes. This destruction is believed to be mediated, at least in part, by TNF-α (Selmaj, et al., supra). TNF-α will initiate apoptosis in perpetuated rat O-2A cells (CG-4) in vitro (Louis, et al., supra). In that study, apoptosis could be blocked by the polypeptide growth factor CNTF (Louis, et al., supra), as well as the antioxidants N-acetylcysteine, vitamin C, and Trolox. TNF-α initiates apoptosis in HOP-1 cells as well.

Therapeutic grafting has particular promise in demyelinating disease such as multiple sclerosis. In the rat oligodendrocyte progenitor cultures that have been grown and expanded in vitro can be engrafted back into the animal. Mice mutant for myelin production can serve as the recipients of these cells, and marked cells can be seen to migrate, engraft, differentiate and myelinate recipient nerve fibers (Espinosa de los Monteros, et al., *Dev. Neurosci.,* 14:98, 1992). Such observations support the prospects of the use of human oligodendrocyte progenitors in grafting, as a therapy in demyelinating disease, and perhaps following trauma to the CNS. Though HOP-1 cells are very similar to rat O-2A cells they bear features, such as growth factor independence, which clearly distinguish them from the rat cells.

Haplotype-matched oligodendrocyte progenitors may be the target of autoimmune attack, just as the native cells are. As such, it may be of value to genetically engineer the donor cells to reduce their expression of Class 1 MHC, for example. As these cells are readily transfected or infected, such manipulations may be feasible in these cells. Genetically manipulated cells would need to be characterized in terms of their state of transformation and tumorigenicity.

Oligodendrocyte progenitor cells might also serve as vehicles for gene therapy. For example, neurotrophic factors or growth factors found to be deficient in some neurodegenerative diseases might be supplemented via the engrafting of genetically engineered producer cells. HOP-1 oligodendrocyte progenitor cells can be selected to be HLA matched to the recipient, and can be genetically manipulated to express the gene of interest. Such cells may serve as vehicles for gene therapy.

The following cell line has been deposited on May 4, 1995, with the American Type Culture Collection, 1301 Parklawn Drive, Rockville, Md., USA (ATCC):

| Deposit | ATCC Accession No. |
|---------|--------------------|
| HOP-1   | CRL 11881          |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture for 30 years from the date of deposit. The bacteria will be made available by ATCC under the terms of the Budapest Treaty and Applicant assures permanent and unrestricted availability of the progeny of the culture to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. § 122 and the Commissioner's rules pursuant thereto (including 37 CFR § 1.14 with particular reference to 886 OG 638). The assignee of the present application has agreed that if the culture deposit should die or be lost or destroyed when cultivated under suitable conditions, it will be promptly replaced on notification with a viable specimen of the same culture. Availability of the deposited strain is not to be construed as a license to practice the invention in contravention of the rights granted under the authority of any government in accordance with its patent laws. Although the invention has been described with reference to the presently preferred embodiment, it should be understood that various modifications can be made without departing from the spirit of the invention. Accordingly, the invention is limited only by the following claims.

We claim:

1. A human cell line having the characteristics of a pre-oligodendroglial stem cell which is essentially free of astrocyte and oligodendrocyte cell surface markers.

2. The cell line of claim 1, wherein the cells are essentially free of cell surface markers GFAP, GalC, O4, ganglioside $GD_3$ and A2B5, but bind to anti-vimentin antibody.

3. The cell line of claim 1, wherein the pre-oligodendroglial stem cell is immortalized.

4. A human cell line having the characteristics of a pre-oligodendroglial stem cell which is essentially free of astrocyte and oligodendrocyte cell surface markers, wherein the cell line is ATCC CRL 11881.

5. The cell line of claim 1, wherein the pre-oligodendroglial stem cell is derived from neural tissue selected from the group consisting of hippocampus, cerebellum, spinal cord, cortex, striatum, basal forebrain, ventral mesencephalon, and locus ceruleus.

6. The cell line of claim 1, wherein the pre-oligodendroglial stem cell further comprises at least one exogenous gene.

7. The cell line of claim 6, wherein the exogenous gene encodes a receptor.

8. The cell line of claim 7, wherein the receptor is selected from the group consisting of receptors which bind adrenaline, noradrenaline, glutamate, serotonin, dopamine, GABA, and acetylcholine.

9. The cell line of claim 6, wherein the exogenous gene encodes a ligand.

10. The cell line of claim 1, wherein the ligand is selected from the group consisting of adrenaline, noradrenaline, glutamate, dopamine, acetylcholine, gamma-aminobutyric acid, and serotonin.

11. A method of producing a human pre-oligodendroglial stem cell in vitro, the method comprising culturing a neural cell in a vessel in a serum-containing basal media wherein a surface in the vessel allows attachment of the neural cell.

12. The method of claim 11, wherein the pre-oligodendroglial stem cell is derived from neural tissue selected from the group consisting of hippocampus, cerebellum, spinal cord, cortex, striatum, basal forebrain, ventral mesencephalon, and locus ceruleus.

13. The method of claim 11, wherein the surface in the vessel is treated with a polybasic amino acid to allow attachment of the neural cell.

14. The method of claim 13, wherein the polybasic amino acid is polyornithine or polylysine.

15. The method of claim 11, wherein the surface in the vessel is treated with an extracellular matrix molecule to allow attachment of the neural cell.

16. The method of claim 15, wherein the extracellular matrix molecule is selected from the group consisting of laminin, collagen and fibronectin.

17. The method of claim 11, wherein the pre-oligodendroglial stem cell is cultured in serum-free media following culture in serum-containing media.

18. A method of producing a human oligodendrocyte in vitro, the method comprising culturing a human pre-oligodendroglial stem cell in a vessel at low density in a serum-free basal media wherein a surface in the vessel allows attachment of the pre-oligodendroglial stem cell.

19. A method of producing a human oligodendrocyte in vitro, the method comprising culturing the human pre-oligodendroglial stem cell ATCC CRL 11881 in a vessel at low density in a serum-free basal media wherein a surface in the vessel allows attachment of the pre-oligodendroglial stem cell.

20. A method of producing a human astrocyte in vitro, the method comprising culturing a human pre-oligodendroglial stem cell in a vessel at low density in a serum-containing basal media wherein a surface in the vessel allows attachment of the pre-oligodendroglial stem cell.

21. A method of producing a human astrocyte in vitro, the method comprising culturing the human pre-oligodendroglial stem cell ATCC CRL 11881 in a vessel at low density in a serum-containing basal media wherein a surface in the vessel allows attachment of the pre-oligodendroglial stem cell.

22. A method for identifying a composition which affects a human pre-oligodendroglial stem cell which comprises:

(a) incubating components comprising the composition and the pre-oligodendroglial stem cell wherein the incubating is carried out under conditions sufficient to allow the components to interact; and (b) measuring the effect on the pre-oligodendroglial stem cell caused by the composition.

23. The method of claim 22, wherein the effect is inhibition of the pre-oligodendroglial stem cell.

24. The method of claim 22, wherein the effect is stimulation of the pre-oligodendroglial stem cell.

25. The method of claim 22, wherein the pre-oligodendroglial stem cell is derived from neural tissue selected from the group consisting of hippocampus, cerebellum, spinal cord, cortex, striatum, basal forebrain, ventral mesencephalon, and locus ceruleus.

26. The method of claim 22, wherein the pre-oligodendroglial stem cell is immortalized.

27. The method of claim 22, wherein the pre-oligodendroglial stem cell further comprises at least one exogenous gene.

28. The method of claim 27, wherein the exogenous gene encodes a receptor.

29. The method of claim 28, wherein the receptor is selected from the group consisting of receptors which bind adrenaline, noradrenaline, glutamate, serotonin, dopamine, GABA, and acetylcholine.

* * * * *